United States Patent [19]

Kennis et al.

[11] Patent Number: 5,482,943
[45] Date of Patent: Jan. 9, 1996

[54] (6-FLUORO-1,2-BENZISOXAZOL-3-YL)-1-PIPERIDINYL-ALKYL-(2,9-DISUBSTITUTED-4H-PYRIDO[1,2-A]PYRIMIDIN-4-ONE) DERIVATIVES

[75] Inventors: Ludo E. J. Kennis, Turnhout; Jan Vandenberk, Beerse; Albertus H. M. T. Van Heertum, Vosselaar, all of Belgium

[73] Assignee: Janssen Pharmaceutica N.V., Beerse, Belgium

[21] Appl. No.: 676,681

[22] Filed: Mar. 28, 1991

[30] Foreign Application Priority Data

Apr. 19, 1990 [GB] United Kingdom ............ 9008850

[51] Int. Cl.⁶ .................. A61K 31/505; C07D 471/04
[52] U.S. Cl. ............................ 514/258; 544/282
[58] Field of Search ................. 544/282; 514/258

[56] References Cited

U.S. PATENT DOCUMENTS 4,485,107 11/1984 Kennis et al. .................. 424/251
4,804,663 2/1989 Kennis et al. .................. 514/258

FOREIGN PATENT DOCUMENTS 0368388 5/1919 European Pat. Off. .
0378255 7/1990 European Pat. Off. .

OTHER PUBLICATIONS

P. A. J. Janssen et al., "Pharmacology of Risperidone . . . ", CA 108: 179958s (1988).
A. A. H. P. Megens et al., "Differential effects of the new anitpsychotic risperidone on large . . . a comparison with haloperidol", CA 109: 122371m (1988).

*Primary Examiner*—Jyothsna Venkat
*Attorney, Agent, or Firm*—Charles J. Metz

[57] ABSTRACT

Novel 2,9-disubstituted-4H-pyrido[1,2-a]pyrimidin-4-ones having the formula

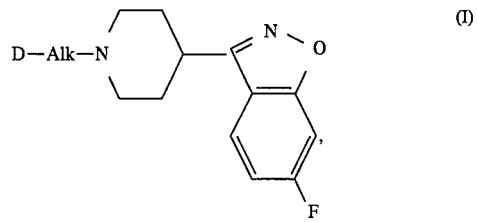

(I)

the pharmaceutically acceptable acid addition salts thereof, and the stereochemically isomeric forms thereof, wherein Alk represents $C_{1-4}$alkanediyl, D is a bicyclic heterocycle of formula

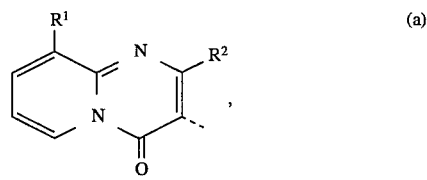

(a)

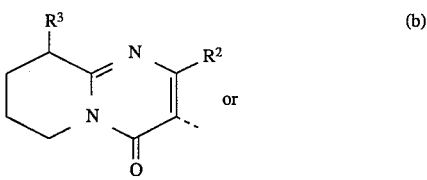

(b)

or

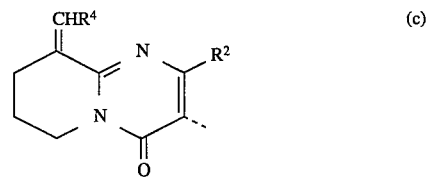

(c)

wherein $R^1$ represents $C_{1-4}$alkyl, hydroxy$C_{1-4}$alkyl, carboxaldehyde, carboxyl, $C_{1-10}$alkylcarbonyloxy$C_{1-4}$alkyl; each $R^2$ represents hydrogen or $C_{1-4}$alkyl; $R^3$ represents $C_{1-4}$alkyl, hydroxy$C_{1-4}$alkyl or methyl substituted with phenyl, 5-methyl-2-furanyl or 3-pyridinyl; and $R^4$ represents $C_{1-3}$alkyl, phenyl, 5-methyl-2-furanyl or 3-pyridinyl.

4 Claims, No Drawings

(6-FLUORO-1,2-BENZISOXAZOL-3-YL)-1-PIPERIDINYL-ALKYL-(2,9-DISUBSTITUTED-4H-PYRIDO[1,2-A]PYRIMIDIN-4-ONE) DERIVATIVES

BACKGROUND OF THE INVENTION

In U.S. Pat. No. 4,804,663 there are described a number of 3-piperidinyl-1,2-benzisoxazoles substituted with a 4H-pyrido[1,2-a]pyrimidin-4-one moiety having antipsychotic activity.

The compounds of the present invention differ therefrom by the specific substitution on the 9-position of the 4H-pyrido[1,2-a]pyrimidin4-one moiety, and their improved antipsychotic properties, in particular their utility in treating acute psychoses.

DESCRIPTION OF THE INVENTION

The present invention is concerned with novel 2,9-disubstituted-4H-pyrido-[1,2-a]pyrimidin-4-ones having the formula

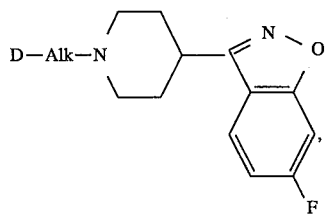

the pharmaceutically acceptable acid addition salts thereof, and the stereochemically isomeric forms thereof, wherein
Alk represents $C_{1-4}$alkanediyl,
D is a bicyclic heterocycle of formula

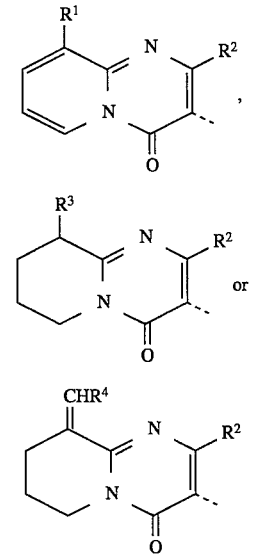

wherein $R^1$ represents $C_{1-4}$alkyl, hydroxy$C_{1-4}$alkyl, carboxaldehyde, carboxyl, $C_{1-10}$alkylcarbonyloxy$C_{1-4}$alkyl; each $R^2$ represents hydrogen or $C_{1-4}$alkyl; $R^3$ represents $C_{1-4}$alkyl, hydroxy$C_{1-4}$alkyl or methyl substituted with phenyl, 5-methyl-2-furanyl or 3-pyridinyl; and $R^4$ represents $C_{1-3}$alkyl, phenyl, 5-methyl-2-furanyl or 3-pyridinyl.

In the foregoing definitions $C_{1-4}$alkanediyl defines bivalent straight and branched chain alkanediyl radicals having from 1 to 4 carbon atoms such as, for example, methylene, 1,2-ethanediyl, 1,3-propanediyl, 1,4-butanediyl and the branched isomers thereof; $C_{1-3}$alkyl defines straight and branched chain saturated hydrocarbon radicals having from 1 to 3 carbon atoms such as, for example, methyl, ethyl, propyl, 1-methylethyl. $C_{1-4}$alkyl defines $C_{1-3}$alkyl radicals and the higher homologs thereof having 4 carbon atoms, e.g. butyl, 1-methylpropyl, 2-methylpropyl and 1,1-dimethylethyl.

An interesting subgroup within the compounds of formula (I) is formed by those compounds wherein D is a bicyclic heterocycle of formula (b) or (c).

Particular compounds are those wherein Alk is 1,2-ethanediyl, $R^2$ is methyl, $R^3$ represents $C_{1-4}$alkyl, hydroxymethyl or methyl substituted with phenyl, 5-methyl-2-furanyl or 3-pyridinyl; and $R^4$ is $C_{1-3}$alkyl, phenyl, 5-methyl-2-furanyl or 3-pyridinyl.

Another particularly interesting subgroup within the compounds of formula (I) is formed by those compounds wherein D is a bicyclic radical of formula (a).

Particular compounds are those compounds of formula (I) wherein Alk is 1,2-ethanediyl, 1,3-propanediyl or 1,4-butanediyl; and/or $R^2$ is hydrogen or methyl.

More particular compounds within the invention are those particular compounds wherein Alk is 1,2-ethanediyl; and/or $R^1$ is $C^{1-4}$alkyl, especially methyl.

The most interesting compounds within the invention are selected from the group consisting of 3-[2-[4-(6-fluoro-1,2-benzisoxazol-3-yl)-1-piperidinyl]ethyl]-2,9 -dimethyl-4H-pyrido[1,2-a]pyrimidin-4-one and the pharmaceutically acceptable acid addition salt forms thereof.

The compounds of this invention may have an asymmetric carbon atom in their structure. The absolute configuration of such a centre may be indicated by the stereochemical descriptors R and S, this R and S notation corresponding to the rules described in Pure Appl. Chem. 1976, 45, 11–30. Unless otherwise mentioned or indicated, the chemical designation of compounds denotes the mixture of all possible stereochemically isomeric forms, said mixtures containing all diastereomers and enantiomers of the basic molecular structure. Stereochemically isomeric forms of the compounds of formula (I) are obviously intended to be embraced within the scope of the invention.

The compounds of formula (I) can generally be prepared by N-alkylating a 3-piperidinyl-1,2-benzisoxazole of formula (II) with an alkylating reagent of formula (III) following an-known N-alkylation procedures.

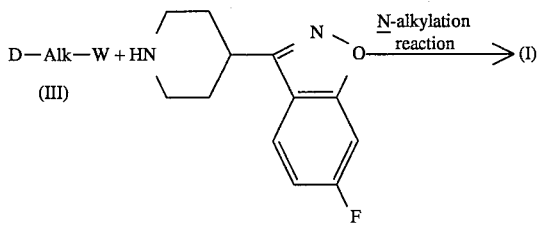

In formula (III) W represents an appropriate reactive leaving group such as, for example, halo, e.g. chloro, bromo or iodo; sulfonyloxy, e.g. methanesulfonyloxy, trifluoromethanesulfonyloxy, benzenesulfonyloxy, 4-methylbenzenesulfonyloxy and the like leaving groups. In case $R^1$ represents hydroxy$C_{1-4}$alkyl, the hydroxyl group may be protected by a protective group such as, for example, phenylmethyl, tertmethylsilyl, tert butyldimethylsilyl and the like. Said N-alkylation reaction can conveniently be carded out by mixing the reactants, optionally in a reaction-inert solvent such as, for example, water; an aromatic solvent, e.g. benzene, methylbenzene, dimethylbenzene, chloro-benzene, methoxybenzene and the like; a $C_{1-6}$alkanol, e.g. methanol, ethanol, 1-butanol and the like; a ketone, e.g. 2-propanone, 4-methyl-2-pentanone and the like; an ester, e.g. ethyl acetate, γ-butyrolactone and the like; an ether, e.g. 1,1'-oxybisethane, tetrahydrofuran, 1,4-dioxane and the like; a dipolar aprotic solvent, e.g. N,N-dimethylformamide, N,N-dimethylacetamide, dimethylsulfoxide, pyridine, 1,3-dimethyl-3,4,5,6-tetrahydro- 2(1H)-pyrimidinone, 1,3-dimethyl-2-imidazolidinone, 1,1,3,3-tetramethylurea, 1-methyl-2-pyrrolidinone, nitrobenzene, acetonitrile and the like; or a mixture of such solvents. The addition of an appropriate base such as, for example, an alkali metal or an earth alkaline metal carbonate, hydrogen carbonate, hydroxide, oxide, carboxylate, alkoxide, hydride or amide, e.g. sodium carbonate, sodium hydrogen carbonate, potassium carbonate, sodium hydroxide, calcium oxide, sodium acetate, sodium methoxide, sodium hydride, sodium amide and the like, or an organic base such as, for example, a tertiary amine, e.g. N,N-diethylethanamine, N-(1-methylethyl)-2-propanamine, 4-ethylmorpholine, 1,4-diazabicyclo[2.2.2octane, pyridine and the like, may optionally be used to pick up the acid which is formed during the course of the reaction. In some instances the addition of an iodide salt, preferably an alkali metal iodide, or a crown ether, e.g. 1,4,7,10,13,16-hexaoxacyclooctadecane and the like, may be appropriate. Stirring and somewhat elevated temperatures may enhance the rate of the reaction; more in particular the reaction may be conducted at the reflux temperature of the reaction mixture. Additionally, it may be advantageous to conduct said N-alkylation under an inert atmosphere such as, for example, oxygen-free argon or nitrogen gas. Alternatively, said N-alkylation may be carried out by applying art-known conditions of phase transfer catalysis reactions. Said conditions comprise stirring the reactants, with an appropriate base and optionally under an inert atmosphere as defined hereinabove, in the presence of a suitable phase transfer catalyst such as, for example, a trialkylphenylmethylammonium, tetraalkylammonium, tetraalkylphosphonium, tetraarylphosphonium halide, hydroxide, hydrogen sulfate and the like catalysts. Somewhat elevated temperatures may be appropriate to enhance the rate of the reaction. In case $R^1$ represents a protected hydroxy$C_{1-4}$alkyl group, the hydroxyl group may be deprotected following art-known methods such as hydrogenolysis or hydrolysis.

In this and the following preparations, the reaction products may be isolated from the medium and, if necessary, further purified according to methodologies generally known in the art such as, for example, extraction, crystallization, trituration and chromatography.

The compounds of formula (I) can conveniently be obtained by the cyclization of an oxime of formula (IV), wherein Y represents a reactive leaving group such as, for example, halo or nitro. Preferably Y represents a halo group and more particularly fluoro.

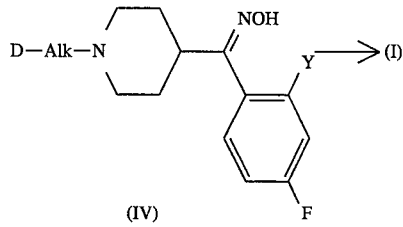

(IV)

Said cyclization reaction of the oxime of formula (IV) may conveniently be conducted by treatment with an appropriate base, preferably in a suitable reaction-inert solvent at temperatures in the range of 20° to 200° C., preferably at 50° to 150° C., and in particular at the reflux temperature of the reaction mixture. Or, if desirable, said base may first be added, preferably at room temperature, whereupon the thus formed oxime salt is cyclized, preferably at an increased temperature and more preferably at the reflux temperature of the reaction mixture. Appropriate bases for said cyclization are, for example, alkali and earth alkaline metal carbonates, hydrogen carbonates, hydroxides, alkoxides or hydrides, e.g. sodium carbonate, sodium hydrogen carbonate, potassium carbonate, sodium hydroxide, sodium methoxide, sodium hydride or organic bases such as amines, e.g. N,N-diethylethanamine, 4-ethylmorpholine and the like bases. Suitable solvents are, for example, water, aromatic hydrocarbons, e.g. benzene, methylbenzene, dimethylbenzene and the like; halogenated hydrocarbons, e.g. dichloromethane, trichloromethane, 1,2-dichloroethane and the like; lower alkanols, e.g. methanol, ethanol, 1-butanol and the like; ketones, e.g. 2-propanone, 4-methyl-2-pentanone and the like; ethers, e.g. 1,4-dioxane, tetrahydrofuran and the like; dipolar aprotic solvents, e.g. N,N-dimethylformamide, N,N-dimethylacetamide, dimethylsulfoxide, 1-methyl- 2-pyrrolidinone and the like, or mixtures of such solvents.

The compounds of formula (I) can also be obtained by cyclizing an activated oxime derivative of formula

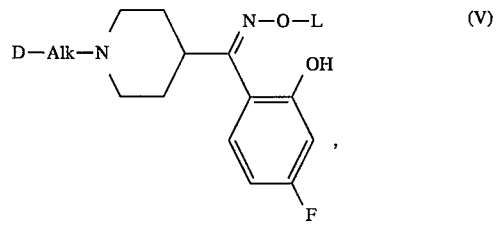

(V)

wherein —O—L represents a reactive leaving group and L is an acid residue and more particularly is formyl, $(C_{1-6}$alkyl or aryl)carbonyl, e.g. acetyl, propionyl, benzoyl and the like; $(C_{1-6}$alkyl or aryl)oxycarbonyl, e.g. methoxycarbonyl, ethoxycarbonyl, (1,1-dimethyl)ethoxycarbonyl, phenyloxycarbonyl and the like; $(C_{1-6}$alkyl or aryl)sulfonyl, e.g. methanesulfonyl, benzenesulfonyl, 4-methylbenzenesulfonyl, 2-naphthalenesulfonyl and the like; N-acylaminocarbonyl, e.g. trichloromethylcarbonylaminocarbonyl and the like. Said cyclization reaction of the activated oxime derivative of formula (V) may conveniently be conducted by treatment with an appropriate base, preferably in a suitable reaction-inert solvent, at temperatures in the range from 20° to 200° C., particularly from 50° to 150° C. and preferably at the reflux temperature of the reaction mixture. In some instances however, it may be advantageous not to add a base to the reaction mixture and to remove the acid liberated during the reaction by destillation at normal pressure or, if desired, at reduced pressure. Alternatively, said cyclization may also be effected by heating the oxime derivative (V) in vacuo without a solvent. Appropriate bases are for example, alkali and earth alkaline metal carbonates, hydrogen carbonates and organic amines, e.g. sodium carbonate, potassium carbonate, sodium hydrogen carbonate, N,H-diethylethanamine, 4-ethylmorpholine, 1,4-diazabicyclo-[ 2.2.2]octane, pyridine and the like bases. Suitable solvents for said eyelization are, for example, aromatic hydrocarbons, e.g. benzene, methylbenzene, dimethylbenzene and the like; ethers, e.g. 1,1'-oxybisethane, 1,1'-oxybisbutane, tetrahydrofuran, 1,4-dioxane, 1,1'-oxybis[2-methoxyethane], 2,5,8,11-tetraoxadodecane and the like; dipolar aprotic solvents, e.g. N,N-climethylformamide, N,N-dimethylacetamide, 1-methyl-2-pyrrolidinone, hexamethylphosphoric triamide, pyridine, acetic anhydride and the like; halogenated hydrocarbons, e.g. trichloromethane, tetrachloromethane, 1,2-dichloroethane, chlorobenzene and the like solvents.

The compounds of formula (I) wherein D is a bicyclic heterocycle of formula (a), said compounds being represented by formula (I-a), can also be prepared following art-known cyclization procedures for preparing pyrimidin-4-ones such as, for example, by reacting an aminopyridine of formula (VII) with a β-dicarbonyl intermediate of formula (VIII), or by cyclizing a reagent of formula (IX) with an enamine of formula (X). In formulae (VIII), (IX) and (X) $R^5$ represents an appropriate reactive leaving group such as, for example, $C_{1-6}$alkyloxy, hydroxy, halo, amino, mono- or di-($C_{1-6}$alkyl)amino and the like.

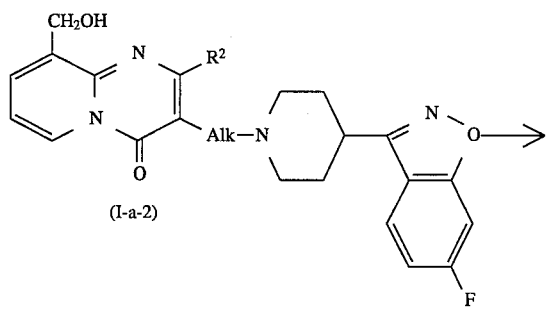

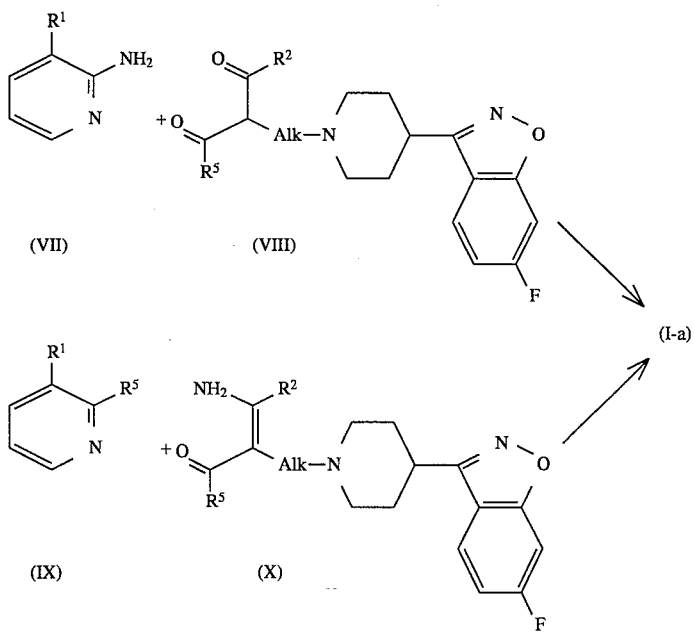

Said cyclization reactions may generally be carried out by stirring the reactants, optionally in the presence of a suitable reaction-inert solvent such as, for example, an aliphatic, alicyclic or aromatic hydrocarbon, e.g. hexane, cyclohexene, benzene and the like; pyridine, N,N-dimethylformamide and the like dipolar aprotic solvents. In order to enhance the rate of the reaction it may be appropriate to increase the temperature, more particularly, it may be recommendable to carry out the reaction at the reflux temperature of the reaction mixture.

The compounds of formula (I-a) wherein $R^1$ represents CHO or COOH can be prepared by oxidation of the corresponding hydroxymethyl compound of formula (I-a-2).

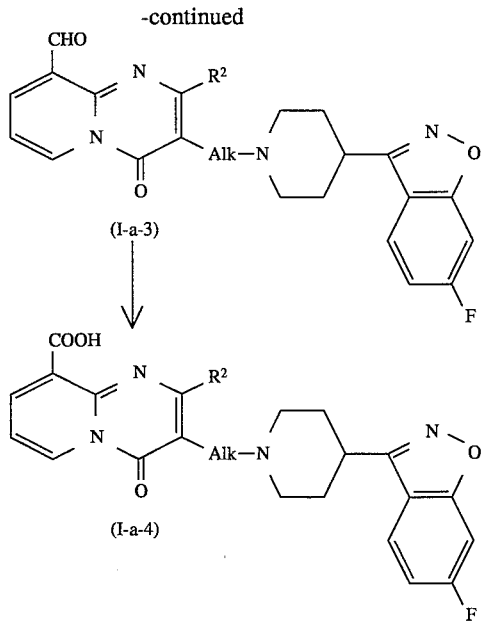

Said oxidation reaction can conveniently be conducted by stirring (I-a-2) in the presence of an oxidizing agent in a suitable solvent.

For example, said oxidation works conveniently with in situ formed adducts of dimethylsulfoxide with dehydrating reagents such as N,N'-methanetetraylbis(cyclohexanamine), acetic anhydride, sulfur(VI)oxide, phosphorus pentoxide, phosgene or oxalyl chloride. The adducts are formed at a low temperature of about −60° C. in an aprotic solvent, preferably dichloromethane, and a solution of the alcohol (I-a-2) is added thereto. After stirring for about 90 minutes at −60° C. to −50° C., a base such as N,N-diethylethanamine is added and the reaction mixture is allowed to reach room temperature. The aldehyde (I-a-3) is isolated employing art-known procedures and may be further oxidized to a carboxylic acid (I-a-4) by treatment with silver(II)oxide in a solvent such as tetrahydrofuran, ethanol and the like, in admixture with water.

The compounds of formula (I) have basic properties and, consequently, they may be convened to their therapeutically active non-toxic acid addition salt forms by treatment with appropriate acids, such as, for example, inorganic acids, such as hydrohalic acid, e.g. hydrochloric, hydrobromic acid and the like, sulfuric acid, nitric acid, phosphoric acid and the like; or organic acids, such as, for example, acetic, propanoic, hydroxyacetic, 2-hydroxypropanoic, 2-oxopropanoic, ethanedioic, propanedioic, butanedioic, (Z)-2-butenedioic, (E)-2-butenedioic, 2-hydroxybutanedioic, 2,3-dihydroxybutanedioic, 2-hydroxy-1,2,3-propanetricarboxylic, methanesulfonic, ethanesulfonic, benzenesulfonic, 4-methylbenzenesulfonic, cyclohexanesulfamic, 2-hydroxybenzoic, 4-amino- 2-hydroxybenzoic and the like acids. Conversely the salt form can be convened into the free base form by treatment with alkali.

The term acid addition salt as used hereinabove also comprises the solvates which the compounds of formula (I) are able to form and said solvates are meant to be included within the scope of the present invention. Examples of such solvates are e.g., the hydrates, alcoholates and the like.

Some of the intermediates and starting materials for use in the foregoing preparations are known compounds, while others are novel. Some intermediates of formula (II) and methods of preparing them are known from U.S. Pat. No. 4,804,663. The alkylating reagents of formula (III) are novel and can be prepared according to art-known methodologies of preparing similar compounds and will be described hereinafter in more detail.

By condensing an optionally protected 2-aminopyridine derivative (VII) with an α-acyl lactone (XI) in the presence of an activating reagent in a suitable reaction-inert solvent, an intermediate of formula (III-a) can be obtained.

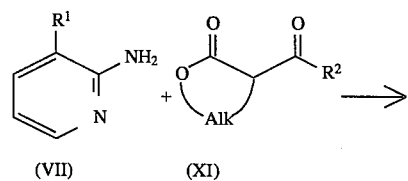

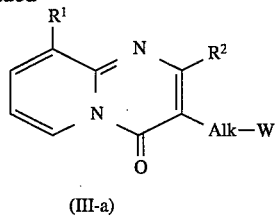

In the formulae (VII), (III-a) and hereinafter whenever expedient, $R^1$ may be protected by a protective group which can be readily removed such as, for example, a hydrogenolyzable group, e.g. phenylmethyl and the like; a hydrolyzable group, e.g. methyl, trimethylsilyl, tert. butyldimethylsilyl and the like. Appropriate activating reagents for said condensation reaction typically are halogenating reagents such as, for example, phosphoryl chloride, phosphoryl bromide, phosphorous trichlofide, thionyl chloride and the like reagents.

Said intermediates of formula (IH-a) can also be obtained by condensing an optionally protected 2-aminopyridine (VII) with a reagent of formula (XII), in the presence of a base in a suitable reaction-inert solvent and subsequently converting the protected alcohol group into a reactive leaving group.

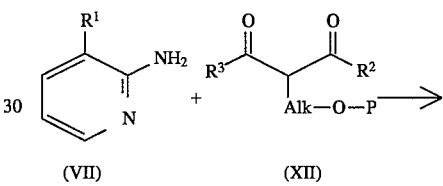

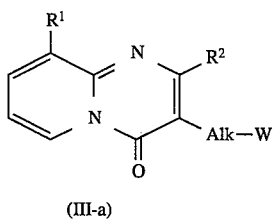

In (XII) P is a readily removable protective group such as, for example an acetal, e.g. a tetrahydropyranyl group and the like protective groups. Said condensation reaction can conveniently be conducted in a solvent such as an alkanol, e.g. methanol, ethanol and the like, a ketone, e.g. 2-propanone, 4-methyl-2-pentanone and the like, an aromatic hydrocarbon, e.g. benzene, methylbenzene and the like. Suitable bases are alkali and earth alkaline metal carbonates, oxides, hydroxides, hydrides or alkoxides, e.g. sodium carbonate, sodium hydroxide, potassium hydroxide, sodium hydride, sodium methoxide, potassium tert butoxide and the like. Subsequently the protective group P is easily removed by acid hydrolysis and the hydroxy group is converted into a leaving group by reaction with a hydrohalic acid, e.g. hydrochloric or hydrobromic acid, a halogenating reagent, e.g. thionyl chloride, phosphorous trichlofide, phosphoryl chloride, phosphorous tribromide and the like, a sulfonylating reagent, e.g. methanesulfonyl chloride, methylbenzenesulfonyl chloride and the like.

Some of the starting materials of formula (III-b) are known and can be prepared according to the procedures described in U.S. Pat. No. 4,485,107. The intermediates of formula (III-b) can also be prepared conveniently from an intermediate of formula (XIII) by condensation with an appropriate aldehyde in the presence of a catalyst such as a Lewis acid, in particular 4-methylbenzenesulfonic acid, in a suitable solvent such as an aromatic hydrocarbon e.g. methylbenzene, dimethylbenzene and the like. The thus obtained intermediate of formula (III-c) can easily be reduced to the intermediates of formula (III-b) by reduction, in particular catalytic hydrogenation.

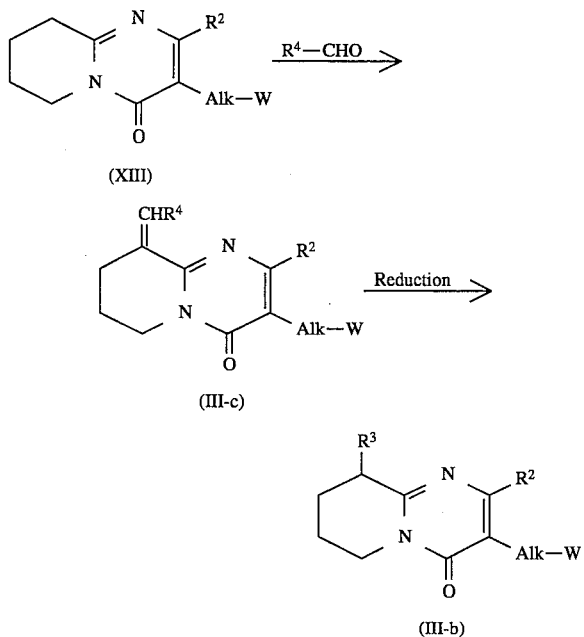

The intermediates of formula (IV) may be prepared by N-alkylating a reagent of formula (III) with an oxime derivative of formula (XIV) following the same procedures as described hereinabove for the preparation of the compounds of formula (I) from the intermediates (II) and (III). The derivatives (XIV) are known from U.S. Pat. No. 4,804,663.

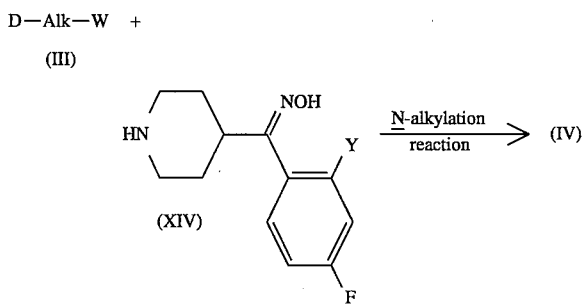

The intermediates of formula (V) may be obtained by reacting an oxime of formula (XV) with an activated acid derivative of formula L-$W^1$,

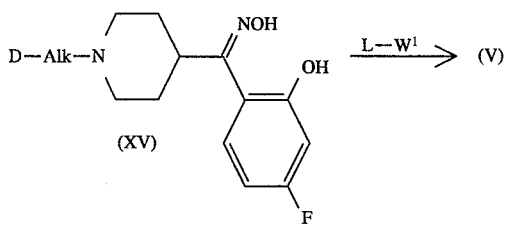

wherein L is an acid residue as defined hereinabove and $W^1$ represents a reactive leaving group such as, for example, halo, (aryl or $C_{1-6}$alkyl)carbonyloxy, (aryl or $C_{1-6}$alkyl)oxy and the like. As typical examples of such reagents there may be mentioned carboxylic acid anhydrides, e.g. acetic anhydride, benzoic anhydride and the like; carboxylic acid halides, e.g. acetyl chloride, benzoyl chloride and the like; carbonochloridates, e.g. methyl, ethyl or phenyl carbonochloridate and the like; di($C_{1-6}$alkyl)carbonates, e.g. dimethylcarbonate, diethylcarbonate and the like. The reaction of the intermediates (XIV) with said activated acid derivatives may be carried out following art-known esterification procedures, e.g. by stirring the reactants at a somewhat elevated temperature, preferably in a reaction-inert solvent such as, for example, an aromatic hydrocarbon, e.g. benzene, methylbenzene and the like; a halogenated hydrocarbon, e.g. dichloromethane, trichloromethane and the like; a ketone, e.g. 2-propanone, 4-methyl-2-pentanone and the like; an ether, e.g. 1,1'-oxybisethane, 1,4-dioxane and the like; a dipolar aprotic solvent, e.g. N,N-dimethylformamide, pyridine and the like solvents. In some instances it may be appropriate to add a suitable base such as, for example, N,N-diethylethanamine, N-(1-methylethyl)-2-propanamine, 4-ethylmorpholine, N,N-dimethyl-4-aminopyridine and the like bases to the reaction mixture.

The intermediate of formula (XV) in turn may be prepared by N-alkylating a reagent of formula (III) with an oxime derivative of formula (XVI)

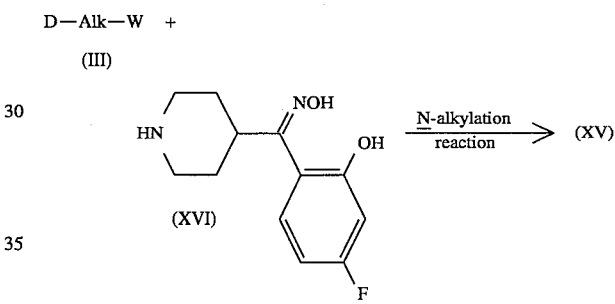

following the same procedures as described hereinabove for the preparation of the compounds of formula (I) from the intermediates (II) and (III).

The compounds of formula (I) and some of the intermediates in the present invention may contain an asymmetric carbon atom. Pure stereochemically isomeric forms of said compounds and said intermediates can be obtained by the application of art-known procedures. For example, diastereoisomers can be separated by physical methods such as selective crystallization or chromatographic techniques, e.g. counter current distribution, liquid chromatography and the like methods. Enantiomers can be obtained from racemic mixtures by first converting said racemic mixtures with suitable resolving agents such as, for example, chiral acids, e.g. tartaric, malic and mandelic acids, camphor sulfonic acid, 4,5-dihydro-1H-2-benzopyran-2-carboxylic acid and the like, to mixtures of diastereomeric salts or compounds; then physically separating said mixtures of diastereomeric salts or compounds by, for example, selective crystallization or chromatographic techniques, e.g. liquid chromatography and the like methods; and finally converting said separated diastereomeric salts or compounds into the corresponding enantiomers by hydrolysis.

Pure stereochemically isomeric forms of the compounds of formula (I) may also be obtained from the pure stereochemically forms of the appropriate intermediates and starting materials, provided that the intervening reactions occur stereospecifically. The pure and mixed stereochemically isomeric forms of the compounds of formula (I) are intended to be embraced within the scope of the present invention.

The compounds of formula (I), the pharmaceutically acceptable acid addition salts and stereochemically isomeric forms thereof, are potent antagonists of neurotransmitters and in particular of dopamine. Antagonizing said neurotransmitter suppresses a variety of phenomena induced by the release, in particular the excessive release, of dopamine. Central dopamine receptor antagonists are known to have neuroleptic properties, for example, they counteract the positive symptoms of schizophrenia, e.g. hallucinations, delusional thinking, severe excitement and unusual behaviour. Therapeutic indications for using the present compounds therefore are mainly in the CNS area, particularly as potent antipsychotic agents and especially as agents useful in treating acute psychoses. The present compounds are particularly effective in treating psychiatric patients suffering from severe agitation and in need of rapid restabilization. Surprisingly, the present compounds are further found to be efficacious in treating patients not responding or responding poorly to administration of other neuroleptica such as haloperidol or risperidone. The present compounds also show central serotonin antagonism. Central acting serotonin antagonists appear to improve the negative symptoms of schizophrenia, e.g. anergy, apathy, social withdrawal and depressive mood, and also appear to reduce the incidence of extrapyramidal side-effects during maintenance therapy with classical neuroleptics, i.e. dopamine antagonists. Combined dopamine-serotonin antagonists are especially interesting as they offer relief of both the positive and negative symptoms of schizophrenia.

The compounds of formula (I) show the additional advantage of also being long acting dopamine antagonists. The potency and long duration of action of the present compounds can easily be demonstrated in a number in vivo tests. For example, the compounds of the present invention inhibit and/or block phenomena or symptoms induced by the dopamine antagonists apomorphine and amphetamine in rats and dogs at low dosages for a relatively long period of time. Hence these compounds only need to be administered at relatively large intervals, the actual time of administration depending on the nature of the compound of formula (I) and on the severity of the condition of the subject to be treated. As a consequence, the present compounds allow for a more efficient therapy and in particular are suitable for intervention in severe, acute situations where a rapid, profound and lasting antipsychotic effect is desired so as to control and restabilize the patient. Further advantages of the present compounds are the excellent bioavailability upon oral administration and the rapid onset of action (<1h).

In view of their useful pharmacological properties, the subject compounds may be formulated into various pharmaceutical forms for administration purposes. To prepare the pharmaceutical compositions of this invention, an effective amount of the particular compound, in acid addition salt or base form, as the active ingredient is combined in intimate admixture with a pharmaceutically acceptable cartier, which may take a wide variety of forms depending on the form of preparation desired for administration. These pharmaceutical compositions are desirably in unitary dosage form suitable, preferably, for administration orally, rectally, percutaneously, or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets. Because of their ease in administration, liquid preparations are especially suited for the treatment of patients during the initial, acute phase of their agitation. On the other hand, during maintenance therapy, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable solutions containing compounds of formula (I) may also be formulated in an oil for prolonged action. Appropriate oils for this purpose are, for example, peanut oil, sesame oil, cottonseed oil, corn oil, soy bean oil, synthetic glycerol esters of long chain fatty acids and mixtures of these and other oils. Injectable suspensions may also be prepared in which case appropriate liquid carriers, suspending agents and the like may be employed. In the compositions suitable for percutaneous administration, the carrier optionally comprises a penetration enhancing agent and/or a suitable wettable agent, optionally combined with suitable additives of any nature in minor proportions, which additives do not cause any significant deleterious effects on the skin. Said additives may facilitate the administration to the skin and/or may be helpful for preparing the desired compositions. These compositions may be administered in various ways, e.g., as a transdermal patch, as a spot-on or as an ointment Acid addition salts of (I) due to their increased water solubility over the corresponding base forms, may obviously be more suitable in the preparation of aqueous compositions.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect, in association with the required pharmaceutical carder. Examples of such dosage unit forms are tablets (including scored or coated tablets), capsules, pills, powder packets, wafers, injectable solutions or suspensions, teaspoonfuls, tablespoonfuls and the like, and segregated multiples thereof.

In view of the usefulness of the subject compounds in the treatment of diseases associated with the release of neurotransmitters, in particular in the treatment of psychotic diseases, it is evident that the present invention provides a method of treating warm-blooded animals suffering from such diseases, in particular psychotic diseases, said method comprising the systemic administration of an antipsychotic amount of a compound of formula (I) or a pharmaceutically acceptable acid addition salt thereof, effective in treating diseases associated with the release of neurotransmitters, in particular psychotic diseases. Those of skill in the treatment of such diseases could easily determine the effective amount from the test results presented hereinafter. In general it is contemplated that an effective antipsychotic amount would be from about 0.0025 to about 4 mg/kg body weight, preferably from about 0.01 mg/kg to about 1 mg/kg body weight, more preferably from about 0.02 mg/kg to about 0.10 mg/kg body weight. The required dose may advantageously be administered as two, three or more sub-doses at appropriate intervals throughout the day. Said subdoses may be formulated as unit dosage forms, for example containing 0.25 to 5 mg, in particular 0.5 to 2 mg of active ingredient per unit dosage form.

The following examples are intended to illustrate and not to limit the scope of the present invention. Unless otherwise stated allparts therein are by weight.

EXPERIMENTAL PART

A. Preparation of the Intermediates

EXAMPLE 1 a) To a solution of 6.2 parts of 2-amino-3-pyridinemethanol in 23.5 parts of N,N-dimethylformamide there were added 6.8 parts of 1H-imidazole and 7.5 parts of chlorodimethyl(1,1-dimethylethyl)silane. The whole was cooled for 10 min in an ice-bath and was stirred overnight at room temperature. The reaction mixture was diluted with 100 parts of water and the product was extracted with 1,1'-oxybisethane (2x). The combined extracts were washed with water and NaCl (sat.), dried, filtered and evaporated, yielding 11.1 parts (93.1%) of 3-[[dimethyl(1,1-dimethylethyl)silyloxy]methyl] -2-pyridinamine (interm. 1).

b) A mixture of 5.5 parts of intermediate (1), 4.93 parts of dihydro-3-(1-oxoethyl)- 2(3H)-furanone, a pinch of 4-methylbenzenesulfonic acid and 34.4 parts of a mixture of xylenes was stirred for 18 hours at reflux temperature using a water separator. After cooling, there were added 26.1 parts of methylbenzene. The whole was washed successively with water, sodium hydrogen sulfite and NaCl (sat.), and was then dried, filtered and evaporated. The residue was stirred in hexane. The solvent was decanted and, after cooling in a mixture of ethanol and dry ice, the precipitate was filtered off and dried, yielding 6.1 parts (68.1%) of 3-[1-[[3-[[dimethyl(1,1-dimethylethyl)silyloxy]methyl] -2-pyridinyl]amino]ethylidene]dihydro-2(3H)-furanone (interm. 2).

c) To a stirred mixture of 2.5 parts of aluminum chloride and 189 parts of 1,2-dichloroethane there were added 5.4 parts of intermediate (2). After heating for ½ hour at 90° C. and subsequent cooling, there were added 599 parts of dichloromethane and 50 parts of water. The whole was filtered and the organic layer of the filtrate was separated, dried, filtered and evaporated. The residue was dissolved in 149 parts of trichloromethane and this solution was washed with NaCl (sat.), dried, filtered and evaporated. The residue was purified by column chromatography (silica gel; CHCl$_3$/hexane/CH$_3$OH 48:50:2). The eluent of the pure fractions was evaporated, yielding 3.0 parts of product. The less pure fractions were chromatographed again (silica gel; CHCl$_3$/CH$_3$OH 99:1), yielding an additional 1.75 parts of product. The combined crops were crystallized from hexane, yielding 2.91 parts (53.8%) of 9-[[dimethyl(1,1-dimethylethyl)silyloxy]methyl]-3-(2 -hydroxyethyl)-2-methyl-4H-pyrido[1,2- a]pyrimidin-4-one (interm. 3).

d) To a cooled (salt/ice-bath) mixture of 0.348 parts of intermediate (3) and 0.98 parts of pyridine there was added a solution of 0.115 parts of methanesulfonyl chloride in 0.196 parts of pyridine. The mixture was left for ½ hour to reach 0° C. and was further stirred for 20 hours at 4° C. There were added 0.084 parts of NaHCO$_3$ while cooling on ice. Stirring was continued for 1½ hour and then the the whole was filtered. The precipitate was rinsed with 1,1'-oxybisethane and the combined filtrates were evaporated. This residue was used without further purification. Theoretical yield: 0.43 pans (100%) of 9-[[dimethyl(1,1-dimethylethyl)silyloxy]methyl]-2-methyl-4-oxo-4H-pyrido[ 1,2-a]pyrimidin-3-ethanol methanesulfonate(ester) (interm. 4).

e) A mixture of 0.426 parts of intermediate (4), 0.257 parts of 6-fluoro-3-(4-piperidinyl)- 1,2-benzisoxazole monohydrochloride, 3.95 parts of methanol and 0.404 pans of N-(1-methylethyl)-2-propanamine was stirred for 68 hours at 60° C. The reaction mixture was evaporated and the residue was partitioned between trichloromethane and water. The organic layer was separated, washed with NaCl (sat.), dried, filtered and evaporated. The residue was purified by column chromatography (silica gel; CHCl$_3$/CH$_3$OH 96:4). The eluent of the desired fraction was evaporated, yielding 0.319 parts (57.9%) of 9-[[dimethyl(1,1-dimethylethyl)silyloxylmethyl]-3-[2-[4-(6-fluoro- 1,2-benzisoxazol- 3-yl)-1-piperidinyl]ethyl]-2-methyl-4H-pyrido[1,2-a]pyrimidin-4-one (interm. 5).

EXAMPLE 2

To a mixture of 53 parts of (Z)-(2,4-difluorophenyl)(4-piperidinyl)methanone, oxime monohydrochloride and 43.5 parts of 3-(2-chloroethyl)-2,9-dimethyl-4H-pyrido[ 1,2-a]-pyrimidin- 4-one in 160 parts of methanol there were added 72 parts of N-(1-methylethyl)- 2-propanamine. After stirring for 44 hours at 60° C., the reaction mixture was diluted with 54 parts of water. At room temperature the precipitate was filtered off, washed with water and dried in vacuo at 50° C., yielding 78.3 parts (98.8%) of (Z)-3-[2-[4-[(2,4-difluorophenyl)(hydroxyimino)methyl]-1-piperidinyl]ethyl]-2,9-dimethyl-4H-pyrido[1,2-a]pyrimidin-4-one (interm. 6).

EXAMPLE 3 a) To a solution of 5.67 parts of 3-(2-chloroethyl)-6,7,8,9-tetrahydro-2-methyl-4H-pyrido[ 1,2-a]pyrimidin-4-one in 43 parts of xylene there were added 2.65 parts of benzaldehyde and 0.7 parts of 4-methylbenzenesulfonic acid. The whole was refluxed for 8 hours using a water separator. After cooling, the precipitate was filtered off and crystallized from 2-propanol, yielding 2.4 parts (30.5%) of product. The mother liquor was evaporated and the residue was purified by column chromatography (silica gel; CHCl$_3$/CH$_3$OH 95:5). The eluent of the desired fraction was evaporated and the residue was crystallized from 2-propanol, yielding an additional 2 parts (25.4%) of product. Total yield: 4.4 parts (55.9%) of (E)-3-(2-chloroethyl)-6,7,8,9-tetrahydro-2-methyl- 9-(phenylmethylene)-4H-pyrido[1,2-a]pyrimidin-4-one; mp. 130.8° C. (interm. 7).

In a similar manner there were also prepared:

(E)-3-(2-chloroethyl)-6,7,8,9-tetrahydro-2-methyl-9-[(5-methyl-2 -furanyl)methylene]- 4H-pyrido[1,2-a]pyrimidin-4-one; mp. 133.1° C. (interm. 8); (E)-9-butylidene-3-(2-chloroethyl)-6,7,8,9-tetrahydro-2-methyl-4H-pyrido[1,2-a]-pyrimidin- 4-one; mp. 76.6° C. (interm. 9); and (E)-3-(2-chloroethyl)-6,7,8,9-tetrahydro-2-methyl-9-(3-pyridinylmethylene)-4H-pyrido[ 1,2-a]pyrimidin-4-one; (interm. 10)

b) A mixture of 3.14 parts of intermediate 7 and 79 parts of methanol was hydrogenated at normal pressure and room temperature with 1 pan of platinum-on-charcoal catalyst 5%. After the calculated amount of hydrogen was taken up, the catalyst was filtered off and the filtrate was evaporated. The residue was converted into the monohydrochloride salt in 2-propanol, yielding 2.1 parts (59.4%) of 3-(2-chloroethyl)-6,7,8,9-tetrahydro-2-methyl- 9-(phenylmethyl)-4H-pyrido

[1,2-a]pyrimidin-4-one monohydrochloride; mp. 181.4° C. (interm. 11).

In a similar manner there was also prepared:

(±)-9-butyl-3-(2-chloroethyl)-6,7,8,9-tetrahydro-2-methyl4H-pyrido[1,2-a]pyrimidin 4-one monohydrochloride; mp. 175.9° C. (interm. 12).

B. Preparation of the Final Compounds

EXAMPLE 4

A mixture of 4.8 parts of 3-(2-bromoethyl)-2,9-dimethyl-4H-pyrido[1,2-a]pyrimidin-4-one, 3.9 parts of 6-fluoro-3-(4-piperidinyl)-1,2-benzisoxazole monohydrochloride, 10 parts of sodium carbonate, a few crystals of potassium iodide and 144 parts of 4-methyl- 2-pentanone was stirred overnight at room temperature. After cooling, the reaction mixture was poured into water. The organic layer was separated, dried, filtered and evaporated. The residue was purified by column chromatography (silica gel; $CH_2Cl_2/CH_3OH$ 95:5). The eluent of the desired fraction was evaporated and the residue was crystallized from acetonitrile, yielding 3 parts (47.6%) of 3-[2-[4-(6-fluoro-1,2-benzisoxazol-3-yl)-1-piperidinyl]ethyl]-2,9-dimethyl-4H-pyrido[1,2-a]-pyrimidin-4-one; mp. 199.9° C. (comp. 1).

In a similar manner there was also prepared:

3-[2-[4-(6-fluoro-1,2-benzisoxazol-3-yl)-1-piperidinyl]ethyl]-6,7,8,9-tetrahydro-2,9-dimethyl-4H-pyrido[1,2-a]pyrimidin-4-one; mp. 171.8° C. (comp. 2)

EXAMPLE 5

A mixture of 78 parts of intermediate (6), 580 parts of methylbenzene and 25 parts of potassium hydroxide in 260 parts of water was stirred for ½ hour at 45°–55° C. and for 3 hours at reflux temperature. After cooling, the organic layer was separated and left to crystallized while cooling on ice. The product was faltered off, washed with methylbenzene and dried at 50° C. in vacuo, yielding 47.7 parts (80%) of 3-[2-[4-(6 -fluoro-1,2-benzisoxazol-3-yl)-1-piperidinyl]ethyl]-2,9-dimethyl-4H-pyrido[1,2-a] pyrimidin-4-one (comp. 1).

EXAMPLE 6 a) To a solution of 0.806 parts of intermediate (5) in 8.9 parts of tetrahydrofuran there were added 1.46 parts of a tetrabutylammonium fluoride solution in tetrahydrofuran 1M. After stirring for 45 min at room temperature, the reaction mixture was evaporated and the residue was diluted with 5 parts of water. The crystallized product was filtered off, washed with water (5x) and 2,2'-oxybispropane (5x) and dissolved in trichloromethane. This solution was washed with NaOH 1N and water and was then filtered. The filtrate was evaporated and the residue was boiled in 2-propanol. The product was filtered off at room temperature and dried in vacuo at 75° C. for 4 hours, yielding 0.348 parts (54.4%) of 3-[2-[4-(6-fluoro-1,2-benzisoxazol-3-yl)-1-piperidinyl]ethyl]-9-(hydroxymethyl)- 2-methyl-4H-pyrido[1,2-a]pyrimidin-4-one; mp. 185.6° C. (comp. 3).

EXAMPLE 7

A mixture of 3.14 parts of intermediate (7), 2.2 parts of 6-fluoro-3-(4-piperidinyl)-1,2 -benzisoxazole, 2.65 parts of sodium carbonate, 94 parts of N,N-dimethylformamide and 0.1 part of potassium iodide was stirred overnight at 80°–90° C. The reaction mixture was poured into water and the product was extracted with methylbenzene. The extract was dried, filtered and evaporated. The residue was purified by column chromatography (silica gel; $CHCl_3/CH_3OH$ 90:10). The eluent of the desired fraction was evaporated and the residue was crystallized from acetonitrile. The product was filtered off and dried, yielding 3.5 parts (70.2%) of (E)-3-[2-[4-(6-fluoro-1,2-benzisoxazol-3-yl)-1 -piperidinyl]ethyl]-6,7,8,9-tetrahydro-2-methyl-9-(phenylmethylene)-4H-pyrido[1,2-a]-pyrimidin- 4-one; top. 160.5° C. (comp. 4).

In a similar manner there were also prepared:

(E)-3-[2-[4-(6-fluoro-1,2-benzisoxazol-3-yl)-1-piperidinyl]ethyl]-6,7,8,9 -tetrahydro-2-methyl-9-[(5-methyl-2-furanyl)methylene]-4H-pyrido[1,2-a]pyrimidin-4-one; mp. 190.0° C. (comp. 5);

3-[2-[4-(6-fluoro-1,2-benzisoxazol-3-yl)-1-piperidinyl]ethyl]- 6,7,8,9-tetrahydro-2-methyl- 9-(phenlmethyl)-4H-pyrido[1,2-a]pyrimidin-4-one; mp. 140.1° C. (comp. 6); 3-[2-[4-(6-fluoro-1,2-benzisoxazol-3-yl)-1-piperidinyl]ethyl]-6,7,8,9-tetrahydro-2-methyl-9-(3-pyridinylmethylene)-4H-pyrido[1,2-a]pyrimidin-4-one; mp. 190.4° C. (comp. 7);

(E)-9-butylidene-3-[2-[4-(6-fluoro-1,2-benzisoxazol-3-yl)-1-piperidinyl]ethyl]- 6,7,8,9-tetrahydro- 2-methyl-4H-pyrido[1,2-a]pyrimidin-4-one; mp. 144.7° C. (comp. 8); and (3S)-9-butyl-3-[2-[4-(6-fluoro-1,2-benzisoxazol-3-yl)-1-piperidinyl]ethyl]-6,7,8,9 -tetrahydro-2-methyl-4H-pyrido[1,2-a]pyrimidin-4-one; mp. 115.7° C. (comp. 9);

EXAMPLE 8

To a stirred solution of 3.23 parts of decanoic acid in 133 parts of dichloromethane under a nitrogen atmosphere, there were added successively 4.32 parts of N,N'-methanetetraylbis(cyclohexanamine), 133 parts of dichloromethane, 5.25 parts of compound 3, 0.225 parts of 4-(1-pyrrolidinyl)pyridine and 66.5 parts of dichloromethane. The whole was stirred for 4 hours at reflux temperature using a water separator and for 24 hours at room temperature. The reaction mixture was diluted with 150 parts of water. The aqueous layer was separated and re-extracted with a mixture of trichloromethane and methanol (95:5). The combined organic layers were dried, filtered and evaporated. The residue was taken up in a mixture of trichloromethane and methanol (97:3). The whole was filtered and the filtrate was eluted over silica gel. The pure fractions were evaporated and the residue was crystallized successively from 2-propanol and from a mixture of 2-propanol and 2,2'-oxybispropane. The product was filtered off and dried in vacuo at 50° C., yielding 5.5 parts (77.6%) of [3-[2-[4-(6-fluoro-1,2-benzisoxazol-2 -yl)-1-piperidinyl] ethyl]-2-methyl-4-oxo-4H-pyrido[1,2-a]pyrimidin-9-yl]methyl decanoate; mp. 111.8° C. (comp. 10).

EXAMPLE 9 a) To a stirred and cooled (–60° C.) amount of 66.5 parts of dichloromethane there were added 1.5 parts of ethanedioyl dichloride and, after stirring for 5 min, dropwise 1.9 parts of dimethyl sulfoxide. Next there were added successively by syringe a suspension of 2.18 parts of compound 3 in 41.3 parts of dimethyl sulfoxide, and after stirring for 1½ hours at –50°/–60° C., 2.6 parts of N,N-diethylethanamine. At room temperature, the reaction mixture was partitioned between water and dichloromethane. The organic layer was separated, washed with water, dried, filtered and evaporated. The residue was stirred in 2-propanol and then purified by column chromatography (silica gel; $CHCl_3/CH_3OH$ 95:5). The eluent of the desired fraction was evaporated, yielding 1.4 parts (64.4%) of 3-[2-[4-(6-fluoro-1,2-benzisoxazol-3-yl)-1-piperidinyl]ethyl]-2 -methyl-4-oxo-4H-pyrido[1,2-a]pyrimidine-9-carboxaldehyde (comp. 11).

b) To a stirred mixture of 1.4 parts of compound 11 and 16.7 parts of ethanol there were added a solution of 1.6 parts of silver nitrate in 2.2 parts of water and, after stirring for 15 min, dropwise a solution of 1.1 parts of potassium hydroxide in 21.2 parts of water. Stirring at room temperature was continued for 2 hours. The reaction mixture was filtered over diatomaceous earth and the precipitate was rinsed with KOH 6%. The combined filtrates were acidified with HCl and the whole was stirred for ½ hour. The precipitate was filtered off, washed with water and converted into the hydrochloride salt in methanol by addition of 2-propanol saturated with HCl. The salt was filtered off and dried overnight at 80° C., yielding 1.12 parts (71.4%) of 3-[2-[4-(6-fluoro-1,2 -benzisoxazol-3-yl)-1-piperidinyl]ethyl]-2-methyl4-oxo-4H-pyrido[1,2-a]pyrimidine-9-carboxylic acid monohydrochloride; mp. >250° C. (decomp.) (comp. 12).

C. Pharmacological Examples

The long acting, central dopamine antagonism of the present compounds can be demonstrated in a number of relevant pharmacological tests such as, for example, the "Apomorphine antagonism in rats" test, the "Amphetamine antagonism in rats" test and the "Apomorphine antagonism test in dogs" test.

EXAMPLE 10

Apomorphine Antagonism in Rats

The test procedure is described in Arch. Int. Pharmacodyn. Ther. 227, 238–253 (1977) and demonstrates the central dopamine antagonistic activity of the tested compounds of formula (I) by preventing apomorphine (1.25 mg/kg iv) induced agitation and stereotypy such as compulsive sniffing, licking and chewing in rats. In Table 1 are listed the $ED_{50}$ values (mg/kg) for inhibition of apomorphine-induced symptoms obtained with compound (1) and the subsequent apomorphine challenge at different intervals (time).

TABLE 1

| Time | $ED_{50}$ (mg/kg) for inhibition |
| --- | --- |
| 0.5 | 0.021 |
| 1 | 0.018 |
| 2 | 0.032 |
| 4 | 0.068 |
| 8 | 0.29 |

EXAMPLE 11

Amphetamine Antagonism in Rats

This test procedure is described in Industrial Pharmacology, Part II, Antidepressants, eds, S. Fielding and H. Lal, p. 125–141, Futura Publishing Company (1975). Solvent (controls) or the test compound (1) were injected sc, followed after 45 min by amphetamine (2.5 mg/kg, sc). Starting 15 min after the amphetamine injection, agitation and consumption of oxygen were evaluated every 15 min over a period of 1 hour. Agitation was scored 3 (pronounced), 2 (moderate), 1 (slight) and 0 (absent), the total score maximally being 4×3=12. Oxygen consumption was measured on a mercury manometer simultaneously. Significant inhibition required a total score for agitation of less than 11 (0.3% in controls) or a final scale reading for oxygen consumption of less than 105 Hg units (1.8% in controls; mean=118 units). Blockade of amphetamine-induced agitation was considered complete at a total score of less than 4 and that of oxygen consumption at a scale reading of less than 90 Hg units (i.e. the agitation score and oxygen consumption level of normal rats which is never observed in amphetamine-treated controls). Listed are the $ED_{50}$ values (mg/kg) obtained with compound (1) and the subsequent amphetamine challenge.

| Amphetamine antagonism | Inhibition | Blockade |
| --- | --- | --- |
| Agitation | 0.014 | 0.064 |
| Oxygen hyperconsumption | 0.057 | 0.19 |

EXAMPLE 12

Apomorphine Antagonism in Dogs

This test is described in Psychopharmacol. 78, 210–213 (1982) and provides—besides a measure of the potency—a good measure of the duration of action of the tested compounds as dopamine antagonists. Apomorphine (0.31 mg/kg, sc; 4 times the $ED_{95}$) induced emesis in all control dogs. At different time intervals before the apomorphine challenge, the dogs were pretreated with different doses (iv, sc or po) of the test compound (1). Complete absence of emesis for 1 hour after the challenge was adopted as the criterion for apomorphine antagonism in dogs. Listed are the $ED_{50}$ values (mg/kg) obtained with compound (1) at different intervals after iv, sc or po administration.

| Time (h) | $ED_{50}$ (iv) | $ED_{50}$ (sc) | $ED_{50}$ (po) |
| --- | --- | --- | --- |
| 0.5 | 0.0012 | 0.0045 | 0.0050 |
| 1 | 0.0011 | 0.0024 | 0.0015 |
| 2 | 0.0012 | 0.0014 | 0.00089 |
| 4 | 0.00079 | 0.00089 | 0.0012 |
| 8 | 0.00089 | 0.0012 | 0.00099 |
| 16 | 0.0012 | 0.0022 | 0.0024 |
| 32 | 0.0029 | 0.0045 | 0.0063 |

D. Composition Examples

The following formulations exemplify typical pharmaceutical compositions in dosage unit form suitable for systemic or topical administration to warm-blooded animals in accordance with the present invention.

"Active ingredient" (A.I.) as used throughout these examples relates to a compound of formula (I), a pharmaceutically acceptable acid addition salt or a stereochemically isomeric form thereof.

EXAMPLE 13

Oral Drops 50 g of the A.I. is dissolved in 0.5 l of 2-hydroxypropanoic acid and 1.5 l of the polyethylene glycol at 60°–80° C. After cooling to 30°–40° C. there are added 35 l of polyethylene glycol and the mixture is stirred well. Then there is added a solution of 1750 g of sodium saccharin in 2.5 l of purified water and while stirring there are added 2.5 l of cocoa flavor and polyethylene glycol q.s. to a volume of 50 l, providing an oral drop solution comprising 1 mg/ml of the A.I. The resulting solution is filled into suitable containers.

EXAMPLE 14

Oral Solution 9 g of methyl 4-hydroxybenzoate and 1 g of propyl 4-hydroxybenzoate are dissolved in 4 l of boiling purified water. In 3 l of this solution are dissolved first 10 g of 2,3-dihydroxybutanedioic acid and thereafter 8 g of the A.I. The latter solution is combined with the remaining pan of the former solution and 12 l of 1,2,3-propanetriol and 3 l of serbitel 70% solution are added thereto. 40 g of sodium saccharin are dissolved in 0.5 l of water and 2 ml of raspberry and 2 ml of gooseberry essence are added. The latter solution is combined with the former, water is added q.s. to a volume of 20 l providing an oral solution comprising 2 mg of the A.I. per teaspoonful (5 ml). The resulting solution is filled in suitable containers.

EXAMPLE 15

Capsules 2 g of the A.I., 6 g sodium lauryl sulfate, 56 g starch, 56 g lactose, 0.8 g colloidal silicon dioxide, and 1.2 g magnesium stearate are vigorously stirred together. The resulting mixture is subsequently filled into 1000 suitable hardened gelatin capsules, each comprising 2 mg of the A.I..

EXAMPLE 16

Film-Coated Tablets

Preparation of Tablet Core

A mixture of 10 g of the A.I., 570 g lactose and 200 g starch is mixed well and thereafter humidified with a solution of 5 g sodium dodecyl sulfate and 10 g polyvinylpyrrolidone (Kollidon-K 90®) in about 200 ml of water. The wet powder mixture is sieved, dried and sieved again. Then there are added 100 g microcrystalline cellulose (Avicel®) and 15 g hydrogenated vegetable oil (Sterorex®). The whole is mixed well and compressed into tablets, giving 10.000 tablets, each comprising 1 mg of the active ingredient.

Coating

To a solution of 10 g methyl cellulose (Methocel 60 HG®) in 75 ml of denaturated ethanol there is added a solution of 5 g of ethyl cellulose (Ethocel 22 cps®) in 150 ml of dichloromethane. Then there are added 75 ml of dichloromethane and 2.5 ml 1,2,3-propanetriol. 10 g of polyethylene glycol is molten and dissolved in 75 ml of dichloromethane. The latter solution is added to the former and then there are added 2.5 g of magnesium octadecanoate, 5 g of polyvinylpyrrolidone and 30 ml of concentrated colour suspension (Opaspray K-1-2109®) and the whole is homogenated. The tablet cores are coated with the thus obtained mixture in a coating apparatus.

EXAMPLE 17

Injectable Solutions 1.8 g methyl 4-hydroxybenzoate and 0.2 g propyl 4-hydroxybenzoate are dissolved in about 0.5 l of boiling water for injection. After cooling to about 50° C. there are added while stirring 4 g lactic acid, 0.05 g propylene glycol and 1 g of the A.I.. The solution is cooled to room temperature and supplemented with water for injection q.s. ad 1l volume, giving a solution of 1 mg A.I. per mi. The solution is sterilized by filtration (U.S.P. XVII p. 811) and filled in sterile containers.

We claim:

1. A compound of the formula:

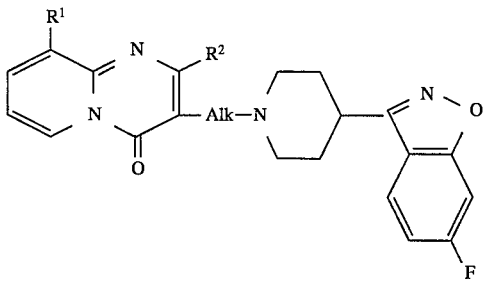

a pharmaceutically acceptable acid addition salt and the stereochemically isomeric forms thereof, wherein:

Alk represents 1,2-ethanediyl [$C_{1-4}$alkanediyl];

$R^1$ represents $C_{1-4}$alkyl; and $R^2$ represents hydrogen or $C_{1-4}$alkyl.

2. A compound according to claim 1 wherein the compound is 3-[2-[4-(6-fluoro-1,2-benzisoxazol- 3-yl)-1-piperidinyl]ethyl]-2,9-dimethyl-4H-pyrido[1,2-a]pyrimidin-4-one or a pharmaceutically acceptable acid addition salt thereof.

3. A pharmaceutical composition comprising an inert carrier and as an active ingredient an effective antipsychotic amount of a compound as claimed in any of claims 2 or 1.

4. A method of treating subjects suffering from psychotic diseases, said method comprising administering to said subjects an effective antipsychotic amount of a compound as claimed in any of claims 2 or 1.

* * * * *